United States Patent [19]
Gibson

[11] Patent Number: 6,063,106
[45] Date of Patent: May 16, 2000

[54] SURGICAL SPACER

[76] Inventor: William Frits Stewart Gibson, 26 Alcock Road, Walmer, South Africa

[21] Appl. No.: 09/156,398

[22] Filed: Sep. 18, 1998

[30] Foreign Application Priority Data

Sep. 19, 1997 [ZA] South Africa .................. 97/8459

[51] Int. Cl.[7] .................................................. A61B 17/04
[52] U.S. Cl. ............................... 606/232; 24/115 R
[58] Field of Search ........................ 606/232; 24/115 R

[56] References Cited

U.S. PATENT DOCUMENTS

| | | | |
|---|---|---|---|
| 65,499 | 6/1867 | Miller | 606/232 |
| 233,475 | 10/1880 | Cook et al. | 606/232 |
| 261,501 | 7/1882 | Vandermark | 606/232 |
| 3,664,345 | 5/1972 | Dabbs et al. | 606/232 |
| 3,910,281 | 10/1975 | Kletschka et al. | |
| 4,291,698 | 9/1981 | Fuchs et al. | 606/232 |
| 5,306,290 | 4/1994 | Martins et al. | 606/232 |

FOREIGN PATENT DOCUMENTS

0520177 A1  12/1992  European Pat. Off. .

*Primary Examiner*—Gary Jackson
*Attorney, Agent, or Firm*—Birch, Stewart, Kolasch & Birch, LLP

[57] ABSTRACT

A surgical spacer 8 is provided which is useful in preventing the formation of granulation tissue or scarring as a result of the suturing of skin tissue in a patient. The spacer comprises a generally disc-shaped body 10 with a top surface 12 and a bottom surface 14. A first pair of spaced apart apertures, 16 through which opposite ends of suture thread passing through a patients skin are threaded are defined in the body 10. A second pair of spaced apart apertures 17 may also be defined in the body 10. A depression is defined in the bottom surface of the body around the apertures to displace them off the surface of the skin when the bottom surface of the spacer is placed in contact with the skin. The suture thread is then knotted against an upper surface of the spacer.

13 Claims, 1 Drawing Sheet

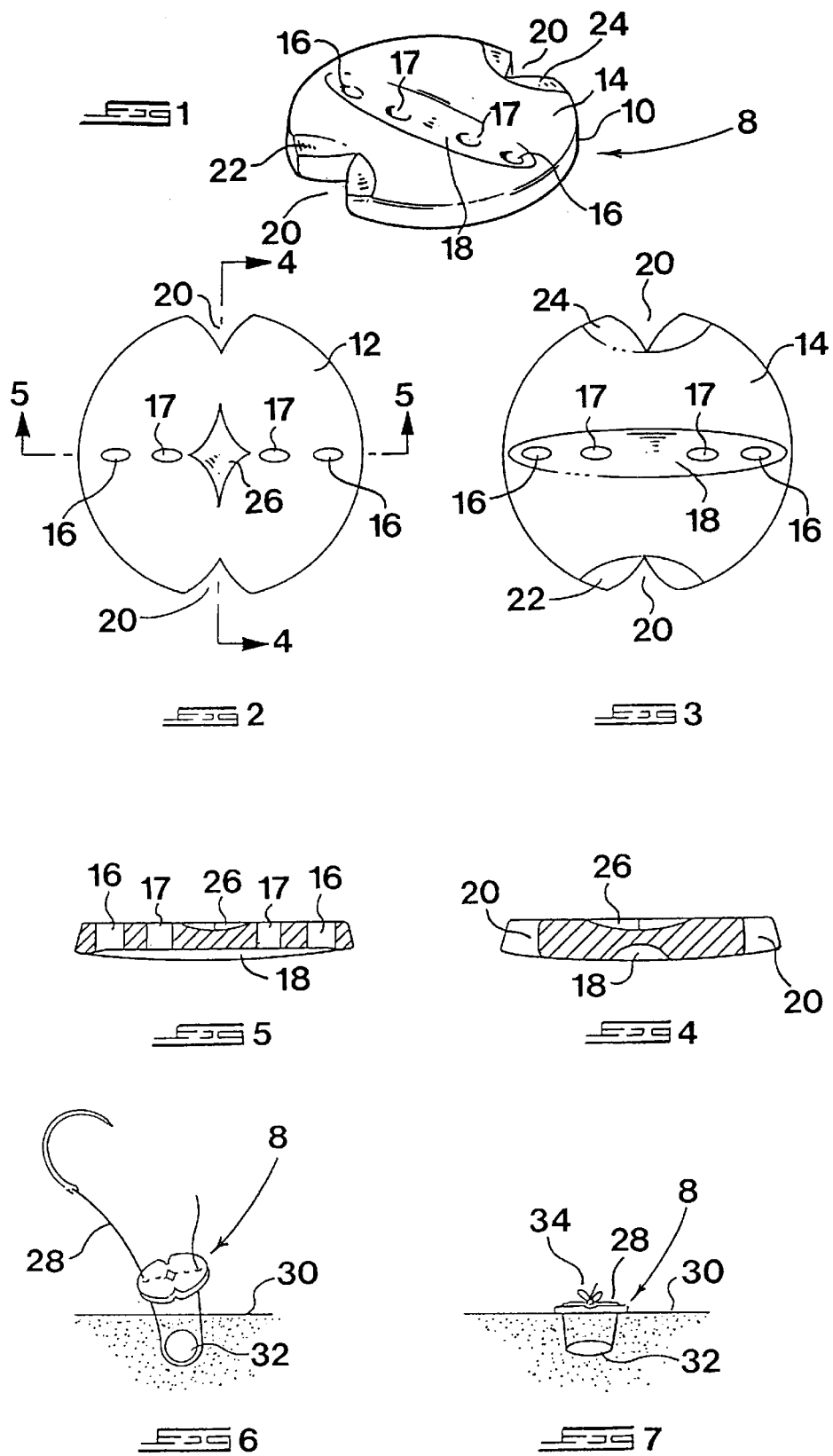

SURGICAL SPACER

BACKGROUND OF THE INVENTION

1. Field of the Invention

This invention relates to a surgical spacer.

2. Description of Related Art

Many surgical techniques involve the suturing of an incision in a patient's skin; they include the elevation of deep structures, temporary diversions and the correction of prolapses. The incisions and subsequent suturing can result in the formation of granulation tissue or scarring on the skin of the patient.

For example, varicose veins may be removed by a surgical ligation technique where an incision is made in the skin of a patient and sutures are inserted around the dilated vessels to restrict blood flow into the vessels. This in turn results in the vessel atrophying.

SUMMARY OF THE INVENTION

According to one aspect of the invention a surgical spacer comprises:

- a body defining top and bottom surfaces, the bottom surface, in use, being placed in contact with a patient's skin;
- an aperture defined in the body through which suture thread can pass;
- a first depression defined in the bottom surface around the aperture to displace the aperture off the skin; and
- a second depression defined in the top surface and shaped to retain a knot in the suture thread therein.

The first depression typically raises the aperture off the skin.

The body is preferably substantially disc-shaped, the bottom surface preferably being convex.

Preferably, a first pair of spaced apart apertures is defined in the body at opposed sides thereof through each of which suture thread can pass.

The first depression in the bottom surface preferably surrounds both opposed spaced apart apertures.

A pair of opposed notches, within each of which a length of suture thread can be received, may be defined in the periphery of the body at opposed sides thereof.

The bottom surface of the body adjacent the respective opposed notches may be cut away to displace the notches off the skin.

The cut away surface typically raises the notches off the skin.

A second pair of spaced apart apertures may be defined in the body between the first pair of spaced apart apertures, through each of which suture thread can pass. The second pair of spaced apart apertures is typically located between the first pair of spaced apart apertures.

The second depression is preferably diamond shaped and located centrally in the top surface of the body, allowing it to retain therein a knot in suture thread passed through any of the aperture, the opposed (spaced apart) apertures or the opposed notches.

According to another aspect of the invention a surgical spacer comprises:

- a body defining top and bottom surfaces, the bottom surface, in use, being placed in contact with a patient's skin;
- a pair of spaced apart apertures defined in the body through which suture thread can pass;
- a first depression defined in the bottom surface around the pair of spaced apart apertures to displace the pair of spaced apart apertures off the skin; and
- a pair of opposed notches defined in the periphery of the body within which a length of the suture thread is receivable.

The spacer is preferably made from a plastics material.

According to another aspect of the invention a method of preventing the formation of granulation and scar tissue on the skin surface in a patient as a result of damage to the skin surface comprises the steps of:

- threading an end of a suture thread through the damaged skin;
- placing a spacer on the surface of the skin, the spacer being adapted such that there is no contact between the spacer and the skin where the suture thread passes through the damaged skin;
- passing the end of the suture thread through at least one aperture or notch in the spacer; and
- knotting the suture against an upper surface of the spacer.

The method may be used to prevent the formation of granulation tissue following surgery to treat chronic ulceration and various types of hernias, the securing of prostheses under the skin and elevating, diverting and retracting of structures under and on the skin.

According to another aspect of the invention a method of suturing a blood vessel in a patient without incising the skin of the patient comprises the steps of:

- sclerosing the blood vessel;
- passing suture thread through the skin and under the blood vessel and passing it back through the skin;
- placing a spacer on the surface of the skin;
- threading an end of the suture through at least one aperture or notch defined in the spacer; and
- knotting the suture against an upper surface of the spacer.

The suture thread is preferably tensioned to apply a constrictive force to the blood vessel.

The knotting of the suture thread against an upper surface of the spacer assists in that the spacer distributes the tension in the suture thread over the skin to prevent the tension in the suture thread from causing deformation of or damage to the skin or underlying tissue.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The spacer is preferably a spacer as described herein.

BRIEF DESCRIPTION OF THE INVENTION

The invention will now be described in more detail, by way of example only, with reference to the accompanying drawings in which:

FIG. 1 is an inverted pictorial view of a spacer of the invention;

FIG. 2 is a top plan view of the spacer;

FIG. 3 is an under plan view of the spacer;

FIG. 4 is a sectional side view on 4—4 in FIG. 2;

FIG. 5 is a sectional side view on 5—5 in FIG. 2;

FIG. 6 is a schematic representation of the use of a spacer of the invention in ligating a blood vessel; and FIG. 7 is a schematic representation of the blood vessel ligated by means of a suture knotted on top of a spacer of the invention.

DETAILED DESCRIPTION OF THE INVENTION

The spacer 8 illustrated in FIGS. 1 to 5 is useful in preventing the formation of granulation tissue or scarring as a result of the suturing of skin tissue in a patient. The spacer comprises a generally disc-shaped body 10 with a top surface 12 and a convex bottom surface 14. A first pair of spaced apart apertures 16 is defied in the body 10 at opposed sides of the body. A generally oval shaped first depression 18 is defined in the bottom surface of the body 10 around both of the apertures 16. The spacer may only contain a single aperture and the suture thread would then be passed through the aperture and around one side of the spacer to be knotted on top of the spacer.

A second pair of spaced apart apertures 17 may also be defined in the body 10. The apertures 17 are located inside the apertures 16, i.e. closer to a central depression 26. This second pair of apertures, which are spaced closer together than the first pair of apertures, allows the spacer to be used in a variety of applications where the size of the wound or the nature of the suturing may differ.

The spacer 8 can be placed between the skin surface and a knot 34 formed in a suture 28 passing through the skin 30 of a patient as shown in FIG. 7. The bottom surface 14 of the spacer is in use placed against the patient's skin and the opposite ends of the suture thread 28 passing through the patient's skin are threaded through the respective apertures 16 or 17. The depression 18 ensures that the mouth of each aperture 16 is raised off the surface of the skin. The displacement of the relatively sharp edges of the apertures from the surface of the skin limits the formation of granulation tissue which could develop within the apertures and around the sutures if the apertures were in contact with the surface of the skin.

The knot 34 is tied against the upper surface of the spacer 8, i.e. it is not directly on the surface of the skin. This allows the tension in the suture to be distributed over the skin surface by the spacer and thus prevents puckering of the skin as well as the formation of granulation tissue or scarring on the surface of the skin. At least some of the tension can also be distributed over the top surface of the spacer itself with the sides of the apertures or notches bearing the lateral forces which would otherwise be applied to the skin by knotting the suture thread. This helps to prevent damage to the skin and underlying tissue.

In addition to the apertures 16 and 17, a pair of channels or notches 20 are defined in the periphery of the body 10 at opposed sides of the body. The notches 20 are sized and shaped to receive and locate a length of the suture 28 therein so that it can be passed to the top surface 12 of the spacer where it is knotted. The distance between these notches 20 is greater than the distance between the apertures 16. This allows the spacer to be used for larger sutures as well without the sutures causing puckering of the skin surface. As a result, the spacer can be used for a number of different applications. The spacer may contain only a single notch and the suture thread would then be passed through the notch and around one side of the spacer to be knotted on top of the spacer.

The bottom surface 14 of the body adjacent to the opposed notches is cut away at areas 22 and 24. These cut away areas perform the same function as the depression 18 and displace the notches off the skin thereby reducing the formation of granulation tissue within the notches.

A second depression 26 is formed centrally in the top surface 12 of the body 10. This depression is diamond shaped so that it effectively retains a knot 34 formed in the suture thread passing through the apertures 16 or 17, or a knot formed in the suture thread passing through the notches 20. It also facilitates the removal of the suture from the incision.

The spacer may be used in a number of different surgical techniques where sutures are passed through the skin to prevent puckering of the skin and the formation of granulation tissue on the skin surface. These include the removal of varicose veins, the treatment of chronic ulceration and different forms of hernias, the attachment of deep structures and the positioning of prostheses under the skin.

The spacer is particularly effective in the ligation of varicose veins. The dilated blood vessels, whether small or large, are tied off by means of a suture 28 passed into the skin 30, around the vessel 32 and back through the skin, as shown in FIGS. 6 and 7. The knot in the suture is not tied directly onto the surface of the skin but instead the suture thread is passed through the spacer 8 and the knot is tied on the top surface of the spacer. The spacer allows a reasonable amount of tension to be placed on the suture thread to apply a constrictive force to the blood vessel. At the same time, it prevents the tension in the suture thread from causing any deformation or damage to the skin surface by applying a lateral force to the skin surface to pucker the skin or damage any underlying tissue. This, combined with sclerotherapy and possibly the use of compression bandages, reduces scarring as a result of the usual surgical technique.

The actual surgical procedure for the ligation of varicose veins using the technique and surgical spacer of the invention involves the following steps: administering intravenous analgesia in the form of either Fentanyl and/or Alfentanil diluted in sterile water through an intravenous line;

cleaning the skin with a mixture of alcohol and antiseptic and drying it;

identifying the offending blood vessels marked with an appropriate surgical marker;

administering local anaesthetic by injection or topical application to the area of intended suturing in the appropriate dose for the patient's weight;

administering an appropriate sclerosing agent via a needle or canula into the offending blood vessel (the solution may include either poly-decanol or various concentrations of salt solution);

inserting a semi-circular reverse cutting needle with a suture material that knots well, such as a monofilament dissolvable suture, for example, through the skin under the blood vessel and passing it back through the surface of the skin;

threading the ends of the suture through the spacer and knotting the suture securely on the top surface of the spacer;

leaving the tied suture on the spacer in situ for a period to effect sclerosis; and covering the spacer and suture by a dressing.

The procedure of tying of major and/or minor blood vessels and related structures may need to be repeated at various intervals during the same treatment or may need to be re-done and another suture inserted at a later time.

At the end of the sclerosing period the spacer and suture are removed and discarded and additional sclerotherapy may follow. Hyperpigmented lesions which develop may be treated with Differen gel® and/or Retin A®. Aloe vera® gel is one of a number of preparations useful for bruising.

The spacer or "button" of the invention may be sold as a kit with instructions in the form of an instruction manual, a computer disk and/or a video for using the spacer in various surgical techniques.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A surgical spacer comprising:
    a body defining top and bottom surfaces, the bottom surface, in use, being placed in contact with a patient's skin;
    at least one aperture defined in the body through which suture thread can pass:
    a first depression defined in the bottom surface around the aperture to displace the aperture off the skin; and
    a second depression defined in the top surface and shaped to retain a knot in the suture thread therein.

2. A surgical spacer according to claim 1, wherein a first pair of spaced apart apertures is defined in the body through each of which suture thread can pass.

3. A surgical spacer according to claim 2, wherein the first depression surrounds the pair of apertures.

4. A surgical spacer according to claim 1, wherein a notch is defined in the periphery of the body within which a length of the suture thread is receivable.

5. A surgical spacer according to claim 4, wherein a pair of opposed notches is defined in the periphery of the body within each of which suture thread is receivable.

6. A surgical spacer according to claim 5, wherein the bottom surface of the body adjacent each notch is cut away to displace each notch off the skin.

7. A surgical spacer according to claim 2, wherein a second pair of spaced apart apertures is defined in the body between the first pair of spaced apart apertures, through each of which suture thread can pass.

8. A surgical spacer according to claim 5, wherein the second depression is diamond shaped and located centrally in the top surface of the body, allowing it to retain therein a knot in suture thread passed through any of the at least one aperture, the spaced apart apertures, or the opposed notches.

9. A surgical spacer comprising:
    a body defining top and bottom surfaces, the bottom surface, in use, being placed in contact with a patient's skin;
    a pair of spaced apart apertures defined in the body through which suture thread can pass;
    a first depression defined in the bottom surface around the pair of spaced apart apertures to displace the pair of spaced apart apertures off the skin; and
    a pair of opposed notches defined in the periphery of the body within which a length of the suture thread is receivable.

10. A method of preventing the formation of granulation and scar tissue on the skin surface in a patient as a result of damage to the skin surface comprising the steps of:
    threading an end of a suture thread through the damaged skin;
    placing a spacer on the surface of the skin, the spacer being adapted such that there is no contact between the spacer and the skin where the suture thread passes through the damaged skin;
    passing the end of the suture thread through at least one aperture or notch in the spacer; and
    knotting the suture thread against an upper surface of the spacer.

11. A method according to claim 10, wherein the spacer is as defined in claim 1.

12. A method of suturing a blood vessel in a patient without incising the skin of the patient comprising the steps of:
    passing suture thread through the skin and under the blood vessel and passing it back through the skin;
    placing a spacer on the surface of the skin;
    threading an end of the suture thread through at least one aperture or notch defined in the spacer and tensioning the suture thread to apply a constrictive force to the blood vessel;
    knotting the suture thread against an upper surface of the spacer so that the spacer distributes the tension in the suture thread over the skin to prevent the tension in the suture thread from causing deformation of or damage to the skin or underlying tissue.

13. A method according to claim 12, wherein the spacer is as defined in claim 1.

* * * * *